United States Patent
Cawood

(10) Patent No.: US 6,352,526 B1
(45) Date of Patent: Mar. 5, 2002

(54) ANTI-REFLUX VALVE FOR COLLECTION BAGS

(75) Inventor: Charles David Cawood, Houston, TX (US)

(73) Assignee: Cawood Family Limited Partnership, Houston, TX (US)

( * ) Notice: Subject to any disclaimer, the term of this patent is extended or adjusted under 35 U.S.C. 154(b) by 0 days.

(21) Appl. No.: 09/439,295

(22) Filed: Nov. 12, 1999

(51) Int. Cl.7 .................................................. A61M 1/00
(52) U.S. Cl. ........................ 604/323; 604/317; 137/223
(58) Field of Search ................................ 604/317, 323, 604/329, 335, 905, 247, 249, 262; 137/223, 846

(56) References Cited

U.S. PATENT DOCUMENTS

| | | |
|---|---|---|
| 4,449,971 A | 5/1984 | Cawood |
| 4,708,167 A | 11/1987 | Koyanagi |
| 4,717,388 A | 1/1988 | Steer et al. |
| 4,723,944 A | 2/1988 | Jensen |
| 4,772,278 A | 9/1988 | Baber |
| 5,188,558 A * | 2/1993 | Barton et al. |
| 5,248,275 A * | 9/1993 | McGrath et al. |
| 5,595,521 A * | 1/1997 | Becker |
| 5,830,780 A | 11/1998 | Dennison et al. |
| 5,860,441 A * | 1/1999 | Garcia |
| 5,934,310 A * | 8/1999 | Littehorn |
| 6,015,601 A * | 1/2000 | Garcia |
| 6,045,542 A | 4/2000 | Cawood |

\* cited by examiner

Primary Examiner—Richard K. Seidel
Assistant Examiner—Kevin C. Sirmons

(57) ABSTRACT

An improved anti-reflux valve is formed as a folded flap of two sheets that are heat sealed along their side edges, folded along their top edges, and free at their lower edges to make a distal opening of the valve. The anti-reflux valve has a channel extending between a point below a valve entry port in one of the sheets down to the distal opening. The ratio of the length of the channel to the width or diameter of the distal opening is 3 to 1, which is an effective ratio to virtually eliminate back flow. The improved anti-reflux valve may be used in a first wall of a urine collection bag to prevent back flow of urine through the valve entry port and into the drainage tube and the bladder.

7 Claims, 1 Drawing Sheet

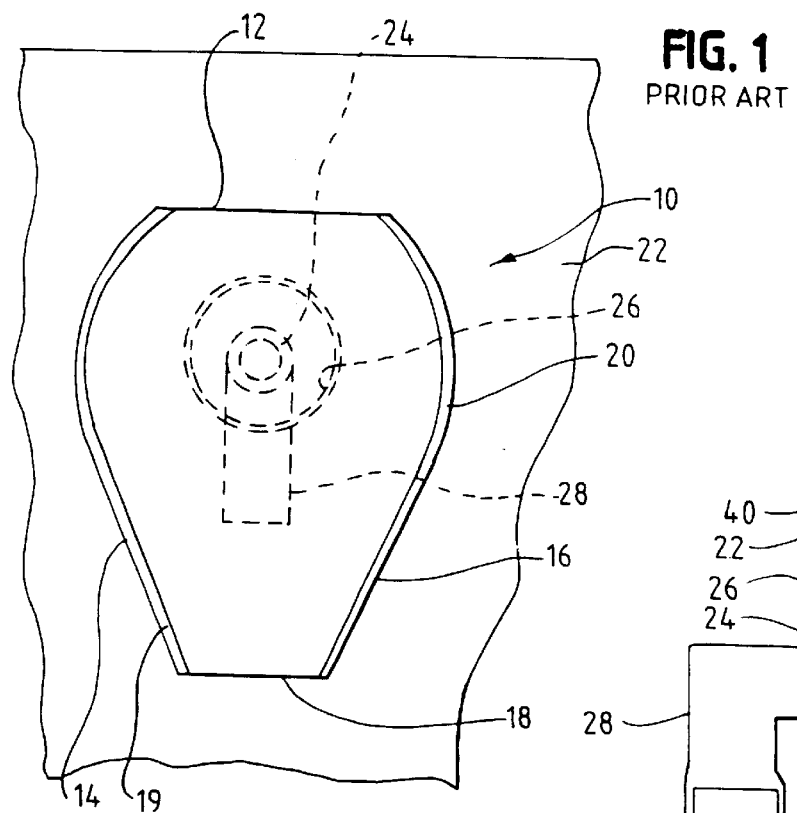
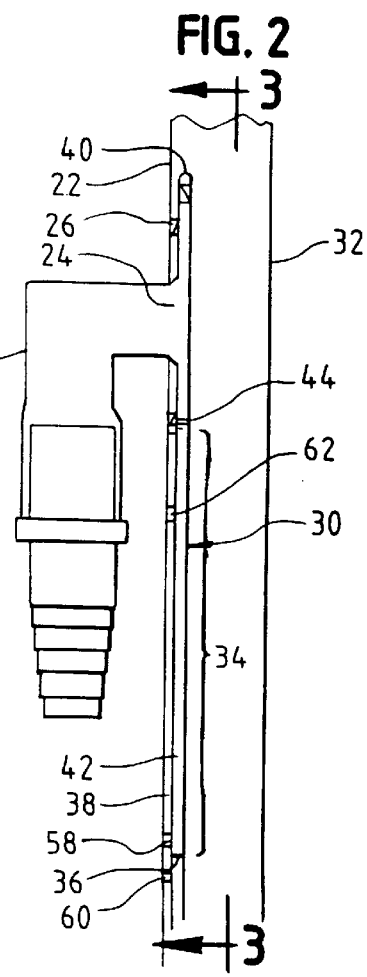
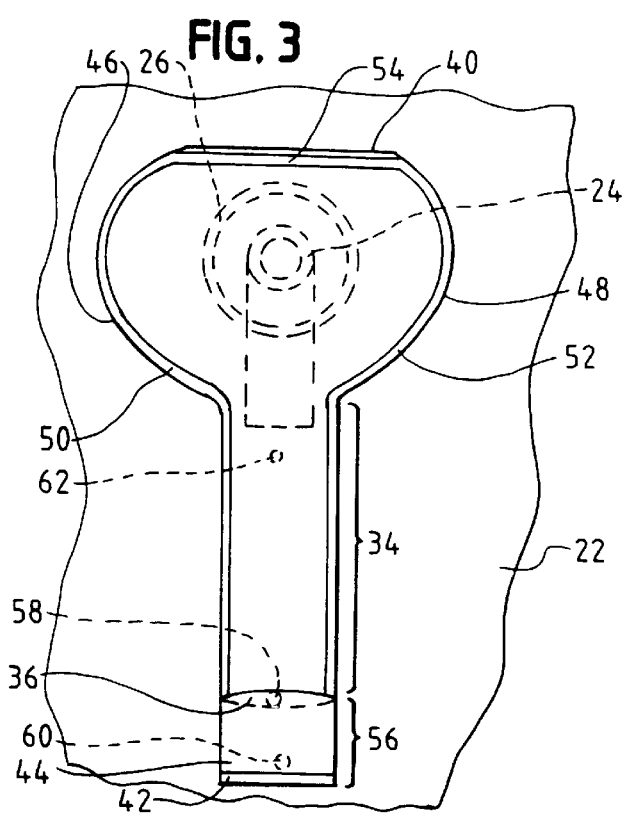

ANTI-REFLUX VALVE FOR COLLECTION BAGS

BACKGROUND

1. Field of the Invention

The present invention relates generally to urine collection bags and, more specifically, to an improved anti-reflux valve for use in a urinary drainage bag to prevent back flow of urine into the drainage tube and the bladder.

2. Description of the Prior Art

In order to facilitate mobility of catheterized patients, urine collection bags are widely available in leg-mounted and abdominally-mounted varieties, as well as bed-side bags for bedfast patients. It is necessary for such urine collection bags to provide a secure connection with the flexible drainage tube that leads from the catheter. However, even with the most secure connection between the drainage tube and the urine collection bag, a frequent problem experienced by wearers of the collection bags is back-flow of urine into the drainage tube, and then the bladder.

An early effort to minimize this problem of back-flow in abdominally worn urine collection bags was to utilize an anti-refluxing flap valve, also known in the art as a non-return valve or flutter valve, and hereinafter referred to simply as an anti-reflux valve, in the form of a pair of inverted V-shaped flexible thermoplastic strips, as described in U.S. Pat. No. 4,449,971. In practice, the inverted U-shaped anti-reflux valve does not function well. In particular, when the urine collection bag is filled and any significant pressure is applied to the bag, pressure is typically applied to the inverted U-shaped valve itself, and it is found that there is unacceptable back-flow.

Later anti-reflux valves for urine collection bags are shown in U.S. Pat. Nos. 4,717,388, 4,772,278, and 4,723,944. The anti-reflux valve in the U.S. Pat. No. 4,717,388 is in the form of a pair of flaps that receive an end of a drainage tube at an upper end of the valve. The two flaps are welded together and taper inwardly along their sides, but are not joined together along their lower ends. The anti-reflux valve of the U.S. Pat. No. 4,772,278 patent is similar to that of the U.S. Pat. No. 4,717,388 patent, but the walls of the valve flare outwardly along the sides toward the lower end. The anti-reflux valve of the U.S. Pat. No. 4,772,278 patent is described to extend below the lower end of a catheter drainage tube by about 65 mm to ensure the valve extends to the region of maximum filling level of the urine collection bag.

The anti-reflux valves described in U.S. Pat. No. 4,723,944 differ from these other prior art anti-reflux valves in several respects. First, the walls of each of the anti-reflux valves of the U.S. Pat. No. 4,723,944 patent extend the full width of the collection bag. Second, instead of a continuous taper, each of the lower side edges or outermost seals of the anti-reflux valves includes an inclined section that leads down to a generally vertical section. One or more additional vertical seals are provided between the outermost vertical seals in the various anti-reflux valves, which form two or more substantially parallel vertical flap valve portions of the anti-reflux valve. Also, the U.S. Pat. No. 4,723,944 patent discusses the use of spot welding to limit the width of the opening of each of the flap valve portions.

It would be desirable for an anti-reflux valve to eliminate virtually all back flow of fluids into drainage tubing, regardless of external pressures applied to the collection bag into which the anti-reflux valve drains. The manner in which the anti-reflux valve of the present invention achieves this desirable result is explained in the following Summary of the Invention, the drawings, and the Detailed Description of the Preferred embodiment.

SUMMARY OF THE INVENTION

Urologists have long understood that in order to prevent back flow of urine in the urinary bladder up into the ureters, each ureteral valve in the bladder has to have a length to diameter ratio of 3 to 1 or more. Specifically, this length to diameter ratio represents the length of the portion of the ureter that is exposed to the mucosa, i.e. the lining of the urinary bladder, to the outer diameter of the opening of the ureter. Otherwise, reflux undesirably occurs, which can cause urinary tract infections, permanent damage to the ureter, and even permanent damage to kidney. Kidney damage is possible because pressure in bladder is much greater than pressures the kidneys are designed to take. Without the adequate anti-reflux result achieved by the 3:1 length to diameter ratio of the portion of each ureter under the mucosa, ordinarily high bladder pressures can be reflected in the kidneys.

The anti-reflux valve of the present invention utilizes this naturally-occurring 3 to 1 ratio to advantageously prevent back flow of urine at the entry port of a urine collection bag. In one embodiment of the anti-reflux valve of the present invention, the anti-reflux valve is formed from a single piece of plastomeric material that is folded over to form a flap. Because of the resulting shape, such anti-reflux valves are also called "duckbill valves." The flap is heat sealed along its side edges, and one half of the flap includes an aperture to receive the distal end or port of the inlet connector for connecting a length of drainage tubing, such as catheter or other body fluid drainage tubing, to a collection bag. In conventional anti-reflux valves, only the side edges of the flap are welded together, leaving a lower open end of the flap that allows drainage into the urine collection bag.

In one typical existing anti-reflux valve, the side edges of the flap are tapered, which results in too low a ratio of effective length to diameter. For example, if the tapered portion of the flap is about 16 millimeters in length, as is typical, with an opening of about 18 millimeters across, the ratio is only 1 to 1.125. External pressures exerted on the urine collection bag can thus undesirably cause back flow of urine up into the valve and even back into the urine drainage tube. Instead, the anti-reflux valve of the first embodiment of the present invention includes a relatively longer flap having an elongated passage formed by parallel heat seals between just below the aperture for the inlet connector and the distal opening at the bottom of the side-sealed elongated passage of the valve.

The elongated passage has a length of about 45 millimeters, and the opening at the bottom of the valve, i.e. the diameter of the passage, is about 15 millimeters. The resulting 3 to 1 length to diameter ratio of this effective portion of the anti-reflux valve thus acts very similar to human ureteral anti-reflux mechanisms. Just as urine is prevented from leaving the urinary bladder and flowing up into the ureter, the elongated passage of the anti-reflux valve prevents urine from entering back into the valve or the drainage tube once it has passed into the urine collection bag.

An additional feature of the present invention is to reduce the opening pressure necessary to initiate the flow of urine, or other fluids, through the anti-reflux valve. A means for reducing the opening pressure is to provide a lowermost unsealed portion of each of the front and rear sheets of the anti-reflux valve below the side heat seals of the flap, i.e. below the distal opening at the bottom of the side-sealed elongated passage. Another means of reducing the opening pressure is to prevent undesired curling of the elongated passage by providing one or more spot welds or heat seal tacks to attach only the rear or front sheet of the elongated passage to a wall of the collection bag. These and other features of the present invention are explained in greater detail in the drawings and the detailed description of the preferred embodiments.

DESCRIPTION OF THE DRAWINGS

FIG. 1 is a rear plan view, broken away, of a front wall of a urine collection device having a prior art anti-reflux valve;

FIG. 2 is a right side view, broken away, of a urine collection bag having an anti-reflux valve of the present invention; and FIG. 3 is a rear plan view of the anti-reflux valve shown in FIG. 2, taken along lines 3—3 of FIG. 2.

DETAILED DESCRIPTION OF THE PREFERRED EMBODIMENTS

Referring first to FIG. 1, an anti-reflux valve 10 found in the prior art is in the form of a length of plastic material that is folded along a top edge at fold 12 to form a teardrop-shaped flap. The side walls 14, 16 are tapered toward a lower open end 18. Heat seals 19 and 20 are provided along the side walls 14 and 16, respectively. The anti-reflux valve 10 is sealed to the rear of a first wall 22 of a urine collection bag at a valve entry port 24, with a reinforcing seal ring 26 to protect the integrity of the valve entry port 24.

In sealing engagement with the valve entry port 24 is an L-shaped tubular member 28 that interfaces with a stepped adapter (not shown) to connect flexible plastic drainage tubing (also not shown) to the anti-reflux valve 10. A typical dimension for the width or diameter of the opening 18 is about 18 millimeters, while the effective length of the tapered portion of the anti-reflux valve is only about 16 millimeters. Thus, the length to diameter ratio of such a prior art anti-reflux valve is only about 1 to 1.125, which is not adequate to prevent back flow of urine into the valve and, detrimentally, back through the valve entry port 24 and into the drainage tubing.

Turning now to FIGS. 2 and 3, an embodiment of the anti-reflux valve 30 of the present invention is shown in association with a urine collection bag having first wall 22 and second wall 32. The anti-reflux valve 30 of this embodiment has an elongated passage 34 extending from below the valve entry port 24 down to a distal opening 36 at the lower end of the valve. The valve 30 is formed from a single length of suitable plastic material 38, e.g., vinyl, folded at an upper edge to form a fold 40, so that the valve 30 has a rear sheet 42 that is immediately adjacent the first wall 22 of the urine collection bag, and a front sheet 44. The valve 30 has side edges 46, 48.

As in the prior art valve 10 shown in FIG. 1, the side edges 46 and 48 are provided with heat seals 50, 52, respectively. Preferably, a substantially horizontal heat seal 54 is provided parallel to and a short distance below the fold 40. It is found that the horizontal heat seal 54 provides increased rigidity to the anti-reflux valve 30, and helps prevent distortion.

Importantly, the elongated passage 34 creates an effective length to diameter ratio of 3 to 1, so that just as the portion of a human ureter within the mucosa of the urinary bladder effectively prevents back flow of urine up into the ureter, the elongated passage 34 prevents back flow of urine into the valve entry port 24. The elongated passage 34 preferably has a length of about 45 millimeters and the diameter of the distal opening 36 of the valve 30 is about 15 millimeters.

Although the anti-reflux valve 30 is shown with the elongated passage 34, it is recognized that there are other variations of anti-reflux valves within the scope of the present invention that achieve the same 3 to 1 ratio of effective length to diameter. For example, it is recognized that one or more additional vertical seals can be provided to existing types of anti-reflux valves, such as the valve 10 shown in FIG. 1, to effectively form two or more parallel one-way flow channels having narrower diameters than the lower open end 18 of the original valve 10. If, for example, one central vertical heat seal is added that has a width of 1 millimeter, the 18 millimeter diameter lower open end 18 is reduced to two 9 millimeter open ends, so an effective length of only about 25 millimeters is required for each resulting one-way channel to achieve the important 3 to 1 ratio of length to diameter. As shown by laboratory testing, these multi-flow channel variations may undesirably cause high "forward pressure" (or opening pressure) to the inflow of urine when the urine collection bag is used.

In order to decrease the amount of forward pressure or opening pressure necessary to first introduce urine through the anti-reflux valve 30 and into the collection bag, it is desirable to have the rear sheet 42 and the front sheet 44 extend downwardly of the heat seals 50, 52 (as shown in FIG. 3). This extra unsealed lowermost vinyl extension portion 56 of the both the front and rear sheets 42, 44 of the anti-reflux valve, i.e. below the end of the vertical portions of heat seals 50, 52, does not detrimentally effect the 3-to-1 ratio of the elongated passage 34 to the diameter of the valve, but does facilitate the beginning of flow of urine into the collection bag by reducing the fluid pressure necessary to separate the front and rear sheets 42, 44 from one another.

In FIG. 3, the extension portion 56 is constructed so that the front sheet 44 terminates just above the rear sheet 42, resulting in an extreme lowermost portion of the rear sheet 42 extending below the front sheet 44. However, the extension portion could instead have both sheets terminate at the same location, or the front sheet could alternatively terminate just below the rear sheet 42. The configuration of the sheets in the unsealed extension portion can take yet other forms as well, and still be effective to reduce the opening pressure of the anti-reflux valve.

In order to further reduce the amount of separating force, i.e. opening pressure or forward pressure, needed for fluid such as urine to spread the rear sheet 42 away from the front sheet 44 and initiate fluid flow into the channel 34, it is most preferable to use one or more heat seal tacks or spot welds 58, 60, 62 to secure only the rear sheet 42 to the first wall 22 of the collection bag. In this manner, the one or more spot welds 58, 60, 62 hold the rear sheet 42, and thus the entire channel 34, in a straight orientation relative to the first wall 22 of the collection bag, so as to prevent undesirable rolling or curling of the channel 34. Rolling or curling of the channel 34 is at least a contributing factor to increasing the separating force necessary to initiate flow into the channel 34. Preferably, at least one of the spot welds 60 is located in the region of the lowermost unsealed portion of the front sheet 42, i.e. below the lower end of heat seals 50, 52, so as to prevent the lowermost unsealed portion of the front sheet 42 from curling and obstructing the distal opening 36.

As a result, if only a small volume of urine were introduced into the valve entry port 24, and the pressure was insufficient to unfurl the channel 34, the urine flow would be obstructed. With the one or more spot welds 58, 60, 62 in place, this problem is advantageously avoided. It is also recognized that by having the one or more spot welds 58, 60, 62 only extend between the rear sheet 42 and first wall 22, as best shown in FIG. 2, these spot welds do not interfere with the desired 3-to-1 length to diameter ratio of the anti-reflux valve of the present invention (because the spot welds do not introduce any physical barriers inside the channel 34 itself).

It is further recognized that if the spot welds were alternatively provided between the front sheet 44 and the second wall 32 of the urine collection bag, the capacity of the collection bag would be undesirably reduced. This is because as such a collection bag is filled with fluid, the one or more spot welds on the front sheet 44 would tend to pull the second wall 32 of the collection bag toward the first wall 22. This arrangement could also have a detrimental effect on the force necessary to introduce fluid into the channel 34, because the orientation of the channel 34 would also be distorted. Similarly, if spot welds were provided between the front sheet 44 and second wall 32 in addition to the one or more spot welds 58, 60, 62 between the rear sheet 42 and first wall 22, the anti-reflux ability of the invention would be undesirably compromised, because as the volume of fluid in the collection bag increased, the walls of the collection bag would expand and the spot welds would tend to pull the rear sheet 42 and front sheet 44 in opposite directions from one another, thereby detrimentally biasing the front and rear sheets of the channel 34 in an open position. This would unacceptably allow backflow of urine into the valve entry port 24 and up into the drainage tubing. For these reasons, it is believed that the most desired placement of the one or more spot welds 58, 60, 62 is only between the rear sheet 42 and first wall 22.

Importantly, the applications for anti-reflux valves of the present invention extend beyond urine collection devices. Anti-reflux valves of the present invention can be utilized wherever liquids or gases are fed through one-way valves. While the present invention has been described with respect to certain embodiments thereof, it is not intended to be limited thereto. It is recognized that variations can be made which are within the scope of the appended claims.

I claim:

1. A collection bag for fluids in combination with an improved anti-reflux valve in control by . . . , said valve formed as a folded-over flap having a front sheet and a rear sheet joined at a fold along an upper edge of each of said front and rear sheets, each of said front and rear sheets having a lower end, a left side edge, and a right side edge, said left side edges being sealed to one another by heat seals, said rear sheet having an aperture therein forming a fluid entry port, and said lower ends defining a distal opening of the anti-reflux valve, the improvement comprising:

a channel extending from a height of said anti-reflux valve below said fluid entry port down to said distal opening, wherein the ratio of the length of said channel to the diameter of said distal opening is 3:1;
   wherein the rear sheet of said anti-reflux valve is adjacent a first wall of said collection bag and said collection bag includes an aperture coextensive with said fluid entry port, with a perimeter of said aperture and said fluid entry port being in a fluid-tight sealed relationship with one another; and
   wherein one or more spot welds are provided along said channel between said rear sheet of said anti-reflux valve and said first wall of said collection bag, whereby said channel is maintained in a straight orientation relative to said first wall of the collection bag.

2. A collection bag for fluids in combination with an improved anti-reflux valve formed as a folded-over flap having a front sheet and a rear sheet joined at a fold along an upper edge of each of said front and rear sheets, each of said front and rear sheets having a lower end, a left side edge, and a right side edge, said left side edges being sealed to one another by heat seals, said rear sheet having an aperture therein forming a fluid entry port, and said lower ends defining a distal opening of the anti-reflux valve, the improvement comprising:

a channel extending from a height of said anti-reflux valve below said fluid entry port down to said distal opening, wherein the ratio of the length of said channel to the diameter of said distal opening is 3:1;
   wherein a portion of each of said front and rear sheets extends downwardly of a lowermost end of each of said heat seals that seal said left side edges and said right side edges, and said lowermost ends of each of said heat seals terminating at said distal opening, thereby forming a lowermost unsealed portion of the anti-reflux valve below the distal opening for reducing opening pressure necessary to initiate the flow of fluid through said distal opening;
   wherein the rear sheet of said anti-reflux valve is adjacent a first wall of said collection bag and said collection bag includes an aperture coextensive with said fluid entry port, with a perimeter of said aperture and said fluid entry port being in a fluid-tight sealed relationship with one another; and wherein one or more spot welds are provided along said channel between said rear sheet of said anti-reflux valve and said first wall of said collection bag, whereby said channel is maintained in a straight orientation relative to said first wall of the collection bag.

3. The combination of the collection bag and anti-reflux valve of claim 2, wherein at least one of said one or more spot welds seals said portion of the rear sheet extending downwardly of the lowermost end of each of said heat seals to said first wall of the collection bag, whereby said portion of the rear sheet is prevented from obstructing said distal opening by curling.

4. An anti-reflux valve having a front sheet having an upper edge, a left side, a right side, and a lower edge;

a rear sheet integral with said front sheet, said rear sheet having an upper edge, a left side, a right side, and a lower edge, said upper edge of the rear sheet connected to said upper edge of the front sheet by a fold;
   a left side heat seal sealing the left side of said front sheet to the left side of said rear sheet;
   a right side heat seal sealing the right sides of said front sheet to the right sides of said rear sheet;
   an aperture in said rear sheet to from a fluid entry port;
   a substantially L-shaped tubular member extending rearwardly of said rear sheet, an open end of said tubular member being in communication with said fluid entry port;
   an additional heat seal sealing said front sheet to said rear sheet and extending from said left side heat seal to said right sides heat seal, said additional heat seal being substantially horizontal and located above said fluid entry port;
   and an elongated channel extending from a height of the anti-reflux valve, said distal opening being defined by said lower edges of the front and rear sheets, wherein the ratio of the length of said elongated channel to the width of said distal opening is 3:1.

5. The anti-reflux valve of claim 4, wherein said additional heat seal is parallel to said fold.

6. The anti-reflux valve of claim 4, in combination with a collection bag for fluids, wherein the rear sheet of said anti-reflux valve is in front of a first wall of said collection bag, said collection bag includes an aperture coextensive with said fluid entry port, with a perimeter of said aperture and said fluid entry port being in a fluid-tight sealed relationship with one another, and said substantially L-shaped tubular member extending through said aperture.

7. The anti-reflux valve of claim 6, wherein one or more spot welds are provided along said channel between said rear sheet of said anti-reflux valve and said first wall of said collection bag, whereby said channel is maintained in a straight orientation relative to said first wall of the collection bag.

* * * * *

UNITED STATES PATENT AND TRADEMARK OFFICE
CERTIFICATE OF CORRECTION

PATENT NO. : 6,352,526 B1
DATED : March 5, 2002
INVENTOR(S) : Charles David Cawood It is certified that error appears in the above-identified patent and that said Letters Patent is hereby corrected as shown below:

Column 2,
Line 4, delete "embodiment", insert -- Embodiment --.

Column 5,
Line 45, delete "in control by . . ., said valve",

Column 6,
Line 56, delete "from", insert -- form --
Line 63, delete "sides", insert -- side --
Line 67, after the word "valve", insert -- below said fluid entry port down to distal opening of the anti-reflux valve, --

Signed and Sealed this

Tenth Day of September, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,352,526 B1 Page 1 of 1
DATED : March 5, 2002
INVENTOR(S) : Charles David Cawood It is certified that error appears in the above-identified patent and that said Letters Patent is hereby corrected as shown below:

<u>Column 3,</u>
Line 29, delete "IIeat", insert -- Heat --

Signed and Sealed this

Twenty-first Day of September, 2004

JON W. DUDAS
*Director of the United States Patent and Trademark Office*